United States Patent [19]

Auer

[11] 4,266,878
[45] May 12, 1981

[54] APPARATUS FOR MEASUREMENT OF SOIL MOISTURE CONTENT

[75] Inventor: Siegfried O. Auer, Bowie, Md.
[73] Assignee: Norlin Industries, Inc., Deerfield, Ill.
[21] Appl. No.: 972,773
[22] Filed: Dec. 26, 1978
[51] Int. Cl.³ .................... G01J 3/38; G01N 21/35
[52] U.S. Cl. ................... 356/419; 250/255; 250/339; 356/51
[58] Field of Search ............... 250/255, 339, 341; 356/407, 419, 420, 445, 446, 51

[56] References Cited

U.S. PATENT DOCUMENTS

| | | | |
|---|---|---|---|
| 3,814,081 | 6/1974 | Mori | 350/96.26 X |
| 3,890,049 | 6/1975 | Collins et al. | 356/445 X |
| 3,901,220 | 8/1975 | Koyasu et al. | 350/96.26 X |
| 3,910,701 | 10/1975 | Henderson et al. | 356/73 X |
| 3,940,608 | 2/1976 | Kissinger et al. | 350/96.24 |

FOREIGN PATENT DOCUMENTS 125631  5/1959  U.S.S.R. .................... 250/255

OTHER PUBLICATIONS

Auer, Siegfried, "Soil Moisture Evaporation Experiments in a Controlled Environment", NASA Final Report under Contract NAS 5-23882, dated Sep. 30, 1977.

Primary Examiner—John K. Corbin
Assistant Examiner—Bruce Y. Arnold
Attorney, Agent, or Firm—Jack Kail; Ronald J. Kransdorf

[57] ABSTRACT

An apparatus for measuring the moisture content of a soil sample at selected depths is disclosed. Light is conducted from a source via a fiber optical cable to a soil probe which is inserted at selected depths into a bore hole formed in the soil sample. Light from the source and reflected light from the soil sample is conducted via fiber optic cables to a reflectometer, which determines reflection factors of the soil sample at three selected infrared wavelengths of a water absorption band. Means are provided to compute the moisture content of the sample at the selected depths from the measured reflectance factors.

12 Claims, 5 Drawing Figures

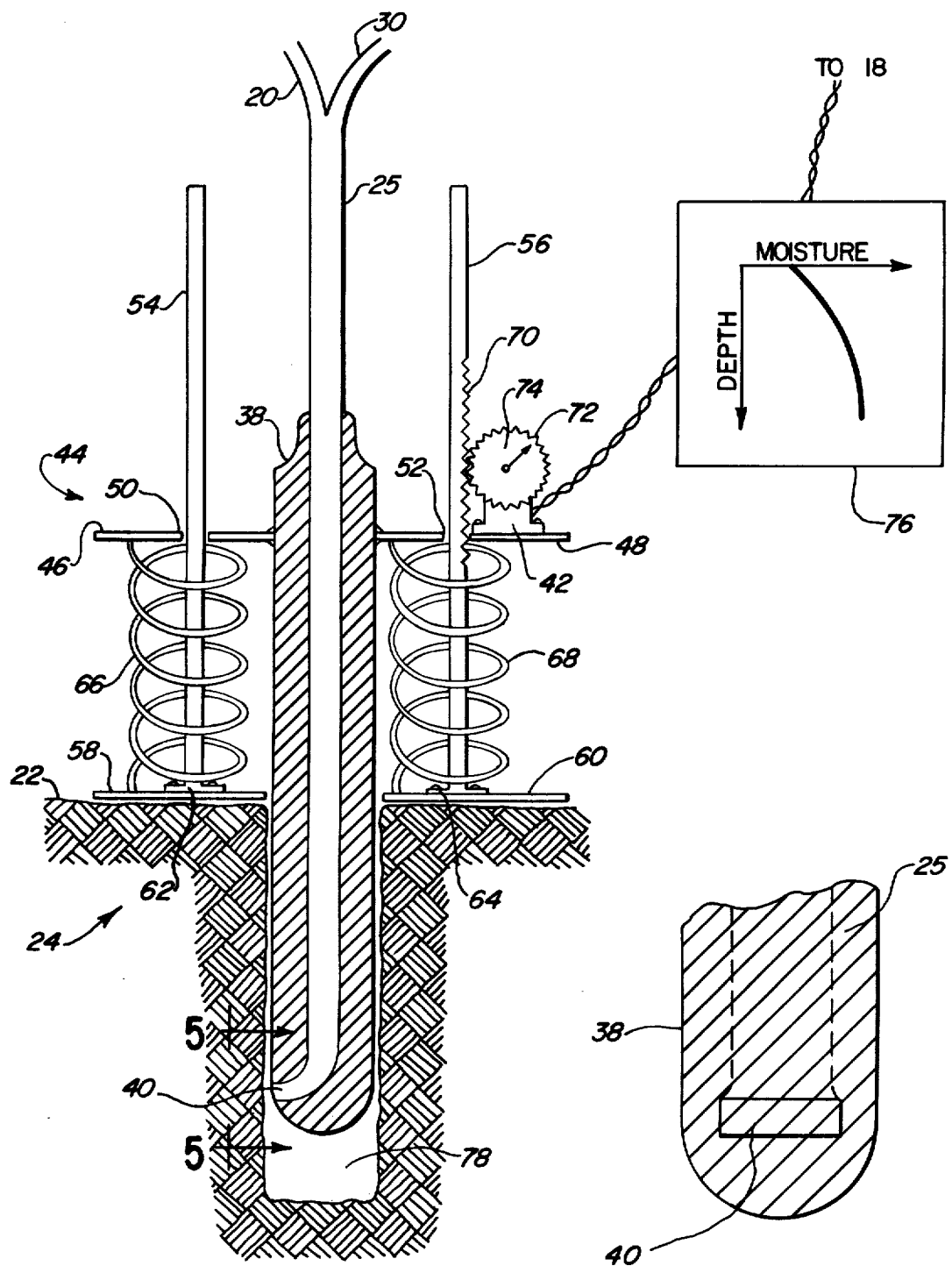

APPARATUS FOR MEASUREMENT OF SOIL MOISTURE CONTENT

BACKGROUND OF THE INVENTION

The present invention relates generally to apparatus for measuring soil moisture and, more particularly, to such apparatus wherein the measurements are achieved non-destructively, in situ, and independently of soil color, soil type, and soil texture.

The moisture content of soil, for example, the soil comprising an agricultural field, is a characteristic vital to the efficient use and preservation of the field. Monitoring the moisture content of the soil is important for enabling the estimation of soil water evaporation and run-off rates, for crop yield forecasting, for scheduling field irrigation and for calibrating remote soil moisture sensing instrumentation. While various techniques have been employed in the past to measure soil moisture, for various generally well-known reasons, none has proven altogether satisfactory.

The standard prior art technique for measuring soil moisture consists of sampling a known volume of soil from the field, weighing the sample, and then drying it after which the dried sample is re-weighed. The weight loss occurring during the drying process is thus equal to the mass of water contained in the original soil sample. The gravimetric soil moisture content may then be calculated by dividing the mass of water attributable to the weight loss by the mass of the dried soil, while the volumetric soil moisture content may be derived by dividing water attributable to the weight loss by the volume of the original moist soil sample. Although the foregoing technique has been widely accepted in the industry, it is characterized by a number of severe shortcomings. Initially, the entire measurement process is relatively costly to implement especially on a continuing basis. Moreover, because of the natural inhomogeneity of the soil, the technique is neither very accurate nor very well reproducible. In addition, due to the requirement of a minimum sample volume of a few cubic centimeters for each measurement, a high soil moisture depth resolution as well as an accurate spatial resolution cannot be achieved utilizing this technique.

Other known methods of measuring soil moisture include techniques implementing the phenomena of neutron scattering, gamma ray absorption, microwave emission and microwave scattering. In the known neutron scattering methods, soil moisture is measured over a large volume so that a high soil moisture depth resolution cannot be achieved. Gamma ray methods of measuring soil moisture involve the use of gamma ray emitters and receivers which are inserted into the soil at different locations. A serious limitation characterizing this method is that the equipment must be calibrated differently for different soil types. To implement the microwave emission method of soil moisture measurement, an independent determination of soil temperature must be made. Although such may be accomplished through a measurement of the emitted thermal radiation in the band from 8 to 14 microns, this additional step is undesirable for obvious reasons. In addition, the soil surface roughness affects the microwave signal in a relatively poorly understood manner further detracting from the desireability of utilizing this technique. Another factor detracting from the microwave emission method concerns the resolution along the soil surface (image resolution) which is severly limited by the wavelength of the microwaves and the antenna size, the image resolution being particularly poor when transmission is from aircraft and spacecraft. Yet further, the microwaves emerge from a soil surface layer whose effective thickness depends on the soil moisture itself. Therefore, the effective thickness of the soil layer being measured is largely unknown. And, while the soil moisture profile of a soil sample may be estimatable by performing measurements on the same sample at several different wavelengths, the corresponding soil temperature profile must also be known. To overcome some of these problems, microwave scattering soil moisture measurement techniques have been developed which are only slightly affected by soil temperatures. However, these techniques are in turn very much disturbed by soil roughness and thus of limited utility.

Various indirect methods of measuring soil moisture are also known in the prior art. Numerous examples of these indirect methods may be found in P. J. Geary's publication "Determination of Moisture in Solids", British Scientific Instrument Association, Report M 24 (1956), the Cable Printing and Publishing Company, Ltd., London. The indirect techniques discussed in this publication as well as other known indirect methods suffer from many of the same drawbacks discussed above which characterize known direct methods of measuring soil moisture.

SUMMARY OF THE INVENTION

It is therefore a basic object of the present invention to provide an improved apparatus for monitoring the moisture content of a soil sample constituting, for example, part of an agricultural field.

It is a further object of the invention to enable the in situ, nondestructive measurement of soil moisture content to a high degree of resolution.

Yet a further object of the invention is to provide an apparatus for measuring soil moisture content which is substantially independent of soil color, soil type and soil texture and which may be conveniently utilized in a timely and cost effective manner.

In accordance with these and other useful objects, the moisture content of a soil sample is determined according to the invention by illuminating the sample with a source of light, monitoring the light reflected from the sample to determine its reflectance factors at selected wavelengths in the infrared spectrum and calculating the soil moisture content based on the thusly determined reflectance factors.

In a preferred embodiment of the invention, light is conducted by a first fiber optics branch from a light source to the soil sample and by a second fiber optics branch to the reference channel of a reflectometer. A third fiber optics branch conducts light reflected from the soil sample to the object channel of the reflectometer. The reflectometer, in association with a computation device, is operable for determining the reflectance factors of the reflected light at selected wavelengths in the infrared spectrum defining a water absorption band thereof, the selected reflectance factors being used to establish the moisture content of the soil sample. Means are also disclosed for measuring the soil moisture content at the surface of a soil sample as well as at selected depths below the surface.

BRIEF DESCRIPTON OF THE DRAWINGS

FIG. 1 graphically depicts an exemplary water absorption band of a soil sample.

FIG. 4 illustrates, partially in cross-section, a soil depth probe useful in association with the embodiment of the invention shown in FIG. 1.

FIG. 5 is a view taken along line 5—5 of FIG. 4.

DESCRIPTION OF THE PREFERRED EMBODIMENT

It is known that water absorption bands exist near 1.45 microns and 1.92 microns in the reflection spectra of all moist soils. Generally, the higher the moisture content of a soil sample, the deeper are its associated water absorption bands, and vice versa. As discussed in more detail hereinafter, the foregoing phenomenon is utilized to particular advantage in accomplishing the objects of the present invention.

Figure 1:
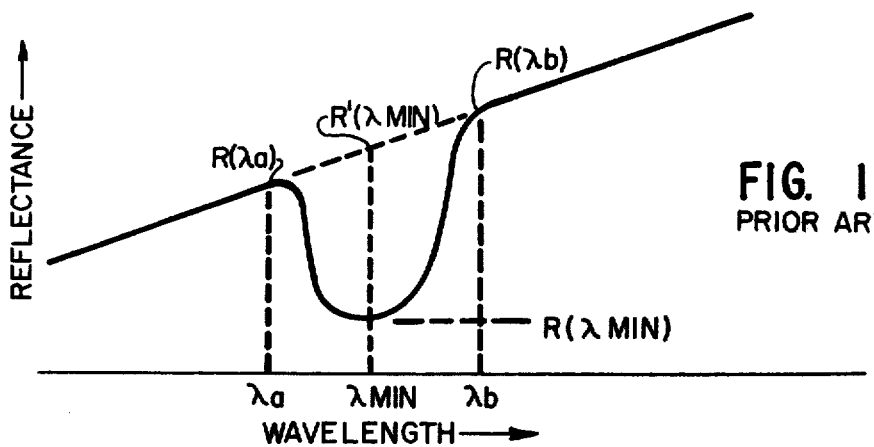

FIG. 1 graphically depicts a typical water absorption band characterizing the reflection spectrum of a soil sample. In this figure, the reflectance of the soil sample is plotted as a function of the wavelength of reflected light. It has recently been found that a direct correlation exists between the moisture content of a soil sample and its associated water absorption bands as generally illustrated in FIG. 1; see the Final Report under NASA contract NAS 5-23882, entitled "Soil Moisture Evaporation Experiments in a Controlled Environment", Report Date—Sept. 30, 1977. In accordance with this report, a typical water absorption band of a soil sample, such as is illustrated in FIG. 1, can be defined by a point of minimum reflectance $R(\lambda min)$ occurring at a wavelength $\lambda min$ and lower and upper band edge reflectances $R(\lambda a)$ and $R(\lambda b)$ occurring at wavelengths $\lambda a$ and $\lambda b$ respectively. In addition, an interpolated reflectance $R'(\lambda min)$ can be postulated as occurring at $\lambda min$, where:

$$R'(\lambda_{min}) = \frac{R(\lambda_b) - R(\lambda_a)}{\lambda_b - \lambda_a} (\lambda_{min} - \lambda_a) + R(\lambda_a). \quad (1)$$

Now, a relative absorption band depth BD can be defined as:

$$BD = 1 - \frac{R(\lambda_{min})}{R'(\lambda_{min})}, \quad (2)$$

where the value of BD varies between zero (0) for minimum band depth and one (1) for maximum band depth. It therefore follows that the relative absorption band depth BD of any given soil sample can be determined on the basis of measurements of the minimum reflectance $R(\lambda min)$ at the wavelength $\lambda min$ together with the band edge reflectances $R(\lambda a)$ and $R(\lambda b)$ at the wavelengths $\lambda a$ and $\lambda b$ respectively.

Water absorption bands of the type discussed above are known to be centered at 0.76, 0.97, 1.19, 1.45, 1.92, 2.7 and 6.3 microns. During the performance of work under the above-mentioned NASA contract, it was observed that correlation between soil moisture content and relative absorption band depth BD was particularly good for the band where $\lambda min = 1.92$ microns, the corresponding band edges occurring at $\lambda a = 1.80$ microns and $\lambda b = 2.05$ microns. In fact, it was observed that the volumetric moisture content M of a wide variety of soil samples was related to the relative absorption band depth BD (for $\lambda min = 1.92$ microns) by the linear expression:

$$M = \frac{BD - 0.055}{2.068}; \quad (3)$$

where BD is given by:

$$BD = 1 - \frac{R(\lambda_{min})}{0.52 \, R(\lambda_a) + 0.48 \, R(\lambda_b)} \quad (4)$$

Significantly, this expression relating volumetric soil moisture content M to relative absorption band depth BD proved relatively accurate independently of such soil sample variables as soil color, particle size and clay content. A somewhat lesser degree of correlation was noted for the band defined by $\lambda min = 1.42$ microns where it was determined that $$M = \frac{BD - 0.030}{0.646}. \quad (5)$$

Figure 2:
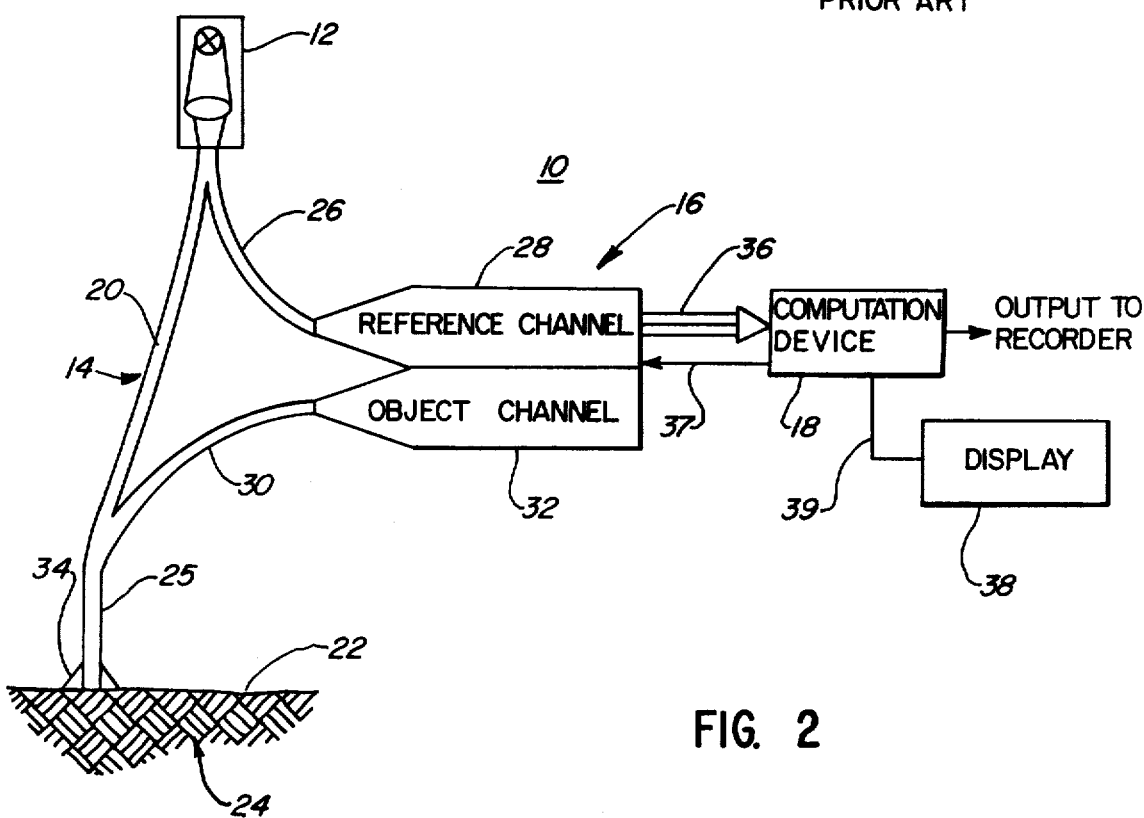
FIG. 2 illustrates, in general block diagram form, a preferred embodiment of the present invention.

A technique for implementing the foregoing discoveries is illustrated in FIG. 2. In this figure, a soil moisture measurement apparatus, identified generally by reference numeral 10, consists essentially of a light source 12, a light transmission system 14, a reflectometer 16 and a computation device 18. Light transmission system 14 includes a first fiber optics branch 20 for conducting light from light source 12 to the surface 22 of a soil sample 24 and a second fiber optics branch 26 for conducting light from light source 12 to the reference channel 28 of reflectometer 16. The conduction of light from source 12 to reference channel 28 by branch 26 serves to automatically compensate reflectometer 16 for fluctuations in the intensity and spectral quality of the light source.

A third fiber optics branch 30, combining with branch 20 in the vicinity of surface 22 for forming a combined branch 25, conducts light reflected from surface 22 to the object channel 32 of reflectometer 16. The soil viewing end of combined branch 25 is surrounded by a funnel-shaped light shield 34 made of, for example, black rubber and designed to keep sunlight and other ambient light from interfering with the operation of light transmitting system 14.

Light source 12 may comprise a conventional tungsten filament incandescent lamp preferably operated from a direct current supply to avoid ac modulation of the light coupled to reflectometer 16 and to soil sample 24. While various other types of light sources may also be used, the spectral properties of the source must be characterized by the production of light energy at various specified wavelengths in the infrared spectrum as described in detail herein. The fiber optics constituting branches 20, 26 and 30 preferably comprise an infrared transmitting material such as those manufactured by Jenaer Glaswerk Schott & Gen., Mainz, West Germany, under the designation IRI. Reflectometer 16 may comprise a Barnes Model 12-550 Mark II or equivalent operable for developing an output signal representative of the ratio of the light flux introduced into object channel 32 by fiber optics branch 30 to the light flux introduced into reference channel 28 by fiber optics branch 26. In addition, reflectometer 16 will typically include means for multiplying the foregoing ratio by a stored factor to compensate for transmission losses in its associated optics system, i.e. light transmission system 14.

In operation, substantially equal densities of light flux are conducted by fiber optics branch 20 to the surface 22 of soil sample 24 and by fiber optics branch 26 to reference channel 28 of reflectometer 16. The light reflected from the soil surface is conducted by fiber optics branch 30 to object channel 32 of reflectometer 16 which, in turn, develops an output data signal on line 36 constituting the reflectance factors of the soil at various selected wavelengths. More particularly, general-purpose reflectometers of the type used herein are normally operable for repeating the reflectance factor determination at a number of selectively different discrete wavelengths. Therefore, during one complete cycle, reflectometer 16 develops a plurality of output reflectance factor related signals on line 36 corresponding to the measured reflectance factors of the sample at a plurality of different wavelengths of the light being processed by the reflectometer.

Computation device 18 is responsive to the output of reflectometer 16 for selecting or processing a limited number of the reflectance factor related signals developed on line 36. More specifically, in the preferred embodiment of the invention, computation device 18 selects reflectance factors $R(\lambda a)$, $R(\lambda min)$ and $R(\lambda b)$ in the infrared spectrum occurring at wavelengths $\lambda a = 1.80$ microns, $\lambda min = 1.92$ micron and $\lambda b = 2.05$ microns while ignoring the reflectance factors at all other wavelengths. Alternatively, reflectometer 16 may be set by normally provided controls such that it measures reflectance factors only at the selected wavelengths $\lambda a$, $\lambda min$, and $\lambda b$. In either event, computation device 18 is designed to initially compute the relative absorption band depth BD for the water absorption band centered at 1.92 microns using expression (4) set forth above. It will be appreciated that, for this computation, the measured value $R(\lambda min)$ corresponds to the reflectance factor at $\lambda = 1.92$ microns while the measured values $R(\lambda a)$ and $R(\lambda b)$ correspond to reflectances at 1.80 microns and 2.05 microns respectively. Next, the computed value for the relative depth BD is utilized by computation device 18 to derive the volumetric moisture content M of the soil sample according to expression (3) above. The thusly computed moisture content of the soil sample may now be supplied to a suitable device 38 over a line 39 for display and/or to an optional recorder for permanent retention.

Figure 3:
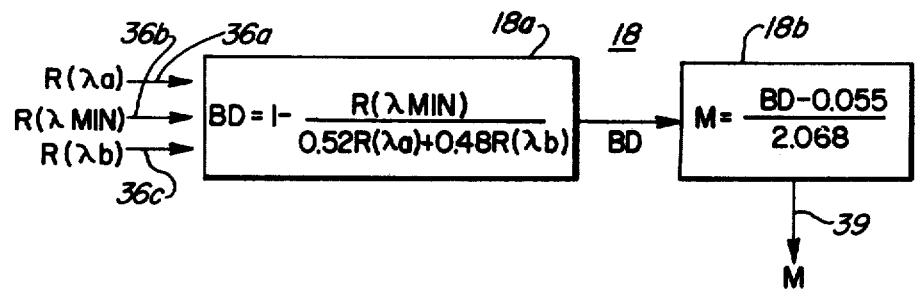
FIG. 3 is a functional block diagram showing an embodiment of the computation device of FIG. 2.

It will be appreciated that the specific implementation of computation device 18 is relatively straight forward and not considered to be a limitation on the present invention. For example, the necessary computations can easily be performed by a suitably configured and scaled "hard wired" electronic circuit as functionally illustrated in FIG. 3. In FIG. 3, the three reflectance factors $R(\lambda a)$, $R(\lambda min)$ and $R(\lambda b)$ are supplied over three separate lines 36a, 36b and 36c to a first section 18a of computation device 18. Section 18a, which may be either analog or digital in nature depending on the type of signals developed by reflectometer 16, includes suitable circuitry for forming an output signal on a line 18c representing the expression for the relative band depth BD. The signal developed on line 18c is then coupled to a second section 18b of computation device 18 which forms the output signal on line 39 representing the volumetric moisture content M of the soil sample. Alternatively, computation device 18 could also be conveniently implemented by a microprocessor programmed for performing the operations illustrated in FIG. 3 to derive the value of volumetric moisture content M. It has also been found that, due to the relative simplicity of the calculations involved, the function of computation device 18 may easily be performed through the use of an equipment operator and a conventional hand-held electronic calculator.

Regardless of the specific implementation of computation device 18, the ultimate result is the derivation of a value for the volumetric moisture content M of the soil sample. The derived value may then be displayed or permanently recorded for future use as desired. Also, to increase the accuracy of the computations, it may be desired to repeat the measurements and calculations a number of times to obtain an average result.

In accordance with the foregoing technique, it will be appreciated that an extremely high degree of spatial resolution is achievable in soil moisture measurements due primarily to the small cross-section of combined fiber optics branch 25 and to the precision with which its soil viewing end is positionable in relation to the soil sample being tested. In this regard, the individual optical fibers of branches 20 and 30 forming combined bundle 25 must be interwoven in a random or in a regular pattern such that the average number density of fibers from either branch is constant over the entire cross-section of the combined bundle. This is necessary to assure homogeneous illumination of the soil sample as well as the conduction of all reflected light from surface 22 to object channel 32 of reflectometer 16. In addition, the fibers of each of the branches 20, 26 and 30 are preferably continuous between their respective distal ends to avoid crosstalk between the branches.

In FIG. 4, apparatus useful in association with the invention for measuring soil moisture depth profiles is shown. In the illustrated apparatus, the combined bundle of optical fibers 25 is embedded in a generally cylindrically-shaped soil probe 38 extending below surface 22 of soil sample 24. The fibers at the viewing end of bundle 25 are bent from the vertical to a horizontal orientation and are arranged such that they terminate in a flat rectangular viewing window 40 (see FIG. 5). A thin transparent teflon film is preferably disposed overlying window 40 on the outside surface of soil probe 38 to provide mechanical protection. Soil probe 38 is operatively connected to a displacement gauge 42 by means of a vertical displacement sensing mechanism 44. Mechanism 44 includes a pair of opposed planar carrier plates 46 and 48 fastened to the probe at its end opposite viewing window 40 for movement therewith. Carrier plates 46 and 48 include apertures 50 and 52 receiving, respectively, a pair of elongate vertically disposed columns 54 and 56. Each column 54, 56 terminates at soil surface 22 in a reference plate 58, 60; the columns being suitably fastened to the reference plates by fastening assemblies 62 and 64. A pair of springs 66 and 68 extend between and are fastened to the interior surfaces of carrier plates 46, 48 and reference plates 58, 60 and are characterized by a suitable degree of resiliency to maintain a predetermined separation between plates 46 and 58 and plates 48 and 60 whereby window 40 of probe 38 is maintained at a fixed distance below surface 22 of soil sample 24. Finally, column 56 includes a plurality of teeth 70 configured for meshing with a plurality of similar teeth 72 disposed about the circumference of a freely rotatable wheel 74 of displacement gauge 42. It will be appreciated that gauge 42 is of the variety adapted for converting rotation of wheel 74 into a corresponding electrical signal where, for example, wheel 74 carries a wiper along a resistive element conneced across a direct current voltage source. The electrical signal developed by displacement gauge 42 is connected to the vertical input of a suitable X-Y plotter 76 whose horizontal input is driven by the output of computation device 18.

In operation, a soil core having a diameter and length slightly greater than the dimension of soil probe 38 is initially removed from soil sample 24 using an earth auger or the like forming a probe receiving bore 78. Soil probe 38 is subsequently inserted in bore 78 with reference plates 58 and 60 of displacement sensing mechanism 44 disposed directly overlying surface 22. In this orientation, carrier plates 46 and 48 will be displaced a predetermined distance above surface 22 causing a corresponding reference signal to be transmitted to the vertical input of X-Y plotter 76 thereby establishing a reference or datum vertical displacement about which subsequent measurements may be performed. The soil moisture content at this reference or datum displacement is determined as previously described and corresponds to the moisture content of the soil opposite window 40. This value is transmitted to the horizontal input of X-Y plotter 76 whose indicating element is correspondingly displaced along the horizontal locus defined by the datum vertical displacement value. Now, assuming that soil moisture content measurements are desired at deeper vertical displacements of probe 38, springs 66 and 68 are compressed lowering window 40 within bore 78. As a result, plate 48 is lowered rotating wheel 74 of displacement gauge 42 and causing a signal representative of the new displacement to be applied to X-Y plotter 76. Simultaneously, soil moisture data at the new depth is supplied to the plotter whose indicating element is correspondigly displaced along the newly established horizontal locus representing the moisture content of the soil at the new vertical displacement. In a similar manner, springs 66 and 68 are expandable for identifying the moisture content of the soil at vertical displacements shallower than the datum level. Thus, by utilizing the illustrated apparatus it will be seen that a soil moisture depth profile along the interior of bore 78 can be easily and conveniently realized.

In an alternate embodiment of the invention, a conventional radiometer, which measures light at the three specified wavelengths, could be used in place of reflectometer 16, assuming that light source 12 is well established. In this case, fiber optics branch 26 connecting light source 12 to reference channel 28 of reflectometer 16 may be omitted. An initial reference reading is obtained by measuring the flux of light reflected from a standard reflector (e.g. teflon powder) held in front of window 40 of soil probe 38. The reflectances at the three specified wavelengths are then determined in relation to the reference reading whereby the volumetric moisture content of the soil may be calculated as previously described.

What has been shown is an improved in situ technique for measuring the moisture content of a soil sample based upon certain characteristics of the water absorption bands of the soil at selected wavelengths. The technique may be conveniently implemented for rapidly providing moisture content measurement without substantially disturbing the soil structure. And, significantly, the results are largely independent of soil color, soil type and soil texture and are achievable to a high degree of spatial resolution.

While particular embodiments of the invention have been shown and described, it will be obvious to those skilled in the art that various changes and modifications may be made without departing from the invention in its broader aspects. For example, it is anticipated that a highly directed beam of light energy may be used in lieu of the optical fibers discussed above. In such a case, the soil sample could be illuminated from a relatively high altitude through the use of an aircraft or the like. Preferably, the measurements would be made at night to reduce the interference of sunlight with the operation of the light transmitting system. The aim of the appended claims, therefore, is to cover all such changes and modifications as fall within the true spirit and scope of the invention.

What is claimed is:

1. Apparatus for monitoring the moisture content of a soil sample comprising:
   a light source for radiating light energy at a plurality of selected wavelengths;
   light transmission means establishing first and second transmission paths each having first and second ends, the first end of said first path being disposed for receiving light radiated from said light source;
   a soil probe insertable in a bore formed in the soil sample, said soil probe including a window for directing light from the second end of said first light transmission path to said soil sample at selected depths within said bore and for directing light reflected from the soil sample to the first end of said second light transmission path;
   displacement measuring means secured to said soil probe for providing an indication of the relative position of said window within said bore;
   means coupled to the second end of said second light transmission path for determining the reflectance factors of said reflected light at said selected wavelengths; and
   means responsive to said reflectance factors and to said position indications for computing the moisture content of the soil sample as a function of the position of said window within said bore.

2. Apparatus according to claim 1 wherein said means for determining comprises a reflectometer having an object channel coupled for receiving light from the second end of said second light transmission path and a reference channel, said light transmission means establishing a third light transmission path coupling light from said light source to said reference channel in an amount substantially equal to that directed by said first light transmission path onto the soil sample.

3. Apparatus according to claim 2 wherein said first, second and third light transmission paths comprise, respectively, first, second and third bundles of continuous fiber optics, said first fiber optics bundle extending between said light source and said soil probe, said second fiber optics bundle extending between said object channel and said soil probe and said third fiber optics bundle extending between said light source and said reference channel.

4. Apparatus according to claim 3 wherein the individual fibers of said first and second fiber optic bundles at their ends opposite said light source and said object channel are mixed with each other, forming a combined fiber optics bundle having a soil viewing end disposed in juxtaposition with said soil probe window.

5. Apparatus according to claim 4 wherein the density of the individual fibers from both said first and second fiber optic bundles is substantially constant over the entire cross-section of said combined bundle.

6. Apparatus according to claim 1 wherein said displacement measuring means includes resilient means normally maintaining said window at a predetermined position relative to said bore, said resilient means being selectively operable for changing the relative position of said window within said bore from said predetermined position.

7. Apparatus according to claim 1 wherein said selected wavelengths are in the infrared spectrum and define the reflectance characteristics of a selected water absorption band of the soil sample.

8. Apparatus according to claim 7 wherein said selected wavelengths occur at the point of minimum reflectance $R(\lambda min)$ and at the points of reflectances $R(\lambda a)$ and $R(\lambda b)$ corresponding to the lower and upper band edges respectively of said selected water absorption band.

9. Apparatus according to claim 8 wherein said reflectances $R(\lambda a)$, $R(\lambda min)$ and $R(\lambda b)$ are determined at the wavelengths 1.80 microns, 1.92 microns and 2.05 microns respectively and wherein said means for computing is configured for determining the volumetric moisture content M of the soil sample according to the expression:

$M = (BD - 0.55)/2.068$, where $BD = (1 - R(\lambda min))(0.52\ R(\lambda a) + 0.48\ R(\lambda b))$.

10. Apparatus for monitoring the moisture content of a soil sample comprising:
- a light source for radiating light energy at least at a plurality of selected wavelengths;
- reflectometer means having an object channel and a reference channel for determining the reflectance factors at said selected wavelengths of light coupled to said object channel relative to light coupled to said reference channel;
- light transmission means comprising a first bundle of continuous fiber optics extending between said light source and said soil sample, a second bundle of continuous fiber optics extending between said optic channel and said soil sample and a third bundle of continuous fiber optics extending between said light source and said reference channel, the individuals fibers of said first and second fiber optic bundles being mixed with each other at their ends opposite said light source and said object channel for forming a combined fiber optics bundle having a soil viewing end disposed in association with said soil sample;
- an elongate soil probe receiving said combined fiber optics bundle, said soil probe being insertable in a bore formed in said soil sample and having a window formed near the distal end thereof, said soil viewing end of said combined bundle being disposed in juxtaposition with said window;
- displacement measuring means secured to said soil probe for providing an indication of the relative position of said window within said bore formed in said soil sample; and
- means responsive to said determined reflectance factors for computing the moisture content of the soil sample.

11. Apparatus according to claim 10 wherein the density of the individual fibers from both said first and second fiber optic bundles is substantially constant over the entire cross-section of said combined bundle.

12. Apparatus according to claim 10 wherein said displacement measuring means includes resilient means normally maintaining said window at a predetermined position relative to said bore, said resilient means being selectively operable for changing the relative position of said window within said bore from said predetermined position.

* * * * *